United States Patent [19]

Summerfield et al.

[11] 4,434,655
[45] Mar. 6, 1984

[54] BLACK POWDER FLAMESPREAD TESTER

[75] Inventors: Martin Summerfield, Princeton; Neale A. Messina, Pennington; Larry S. Ingram, Cranbury, all of N.J.

[73] Assignee: The United States of America as represented by the Secretary of the Army, Washington, D.C.

[21] Appl. No.: 355,816

[22] Filed: Mar. 8, 1982

[51] Int. Cl.³ ............................................... G01L 5/14
[52] U.S. Cl. ............................................ 73/167; 73/35
[58] Field of Search ...................................... 73/167, 35

[56] References Cited

U.S. PATENT DOCUMENTS

| | | | |
|---|---|---|---|
| 2,920,479 | 1/1960 | Kane | 73/167 |
| 3,201,973 | 8/1965 | Fitzgerald | 73/35 |
| 3,685,347 | 8/1972 | Hildebrant | 73/35 |
| 3,946,607 | 3/1976 | Panella | 73/167 |

Primary Examiner—Charles Frankfort
Assistant Examiner—Denis E. Corr
Attorney, Agent, or Firm—Robert P. Gibson; Anthony T. Lane; Max Yarmovsky

[57] ABSTRACT

A black powder flamespread tester is disclosed in which powder to be qualified is packed in a sample tube provided with a plurality of sight holes. Light sensors are disposed adjacent each sight hole and emit signals upon flame front passage of the sight hole. The sample tube is removably secured to an ignition head which contains an electrically actuated pyrotechnic squib. The squib discharges gases into a transition chamber from which the gases pass through orifices in an orifice plate, through a void volume into the black powder bed, which ignites the black powder. The ignition head is removably secured to a tester chamber in which the sample holder is received. Light sensors are housed in a separate fin which is removably received in an aperture in the tester chamber wall. After the squib gas ignites the powder bed, the output signal of each light sensor increases to saturation as the flame front passes its respective sight hole. The output signal from each light sensor is conditioned and summed to form one output signal. A plot of the summed output signal versus time is prepared, which shows the time of passage of the flame front through the black powder from each light sensor to the next. The flamespread rate is determined by dividing the known distance between light sensors by the time of passage of the flame front between respective light sensors.

21 Claims, 5 Drawing Figures

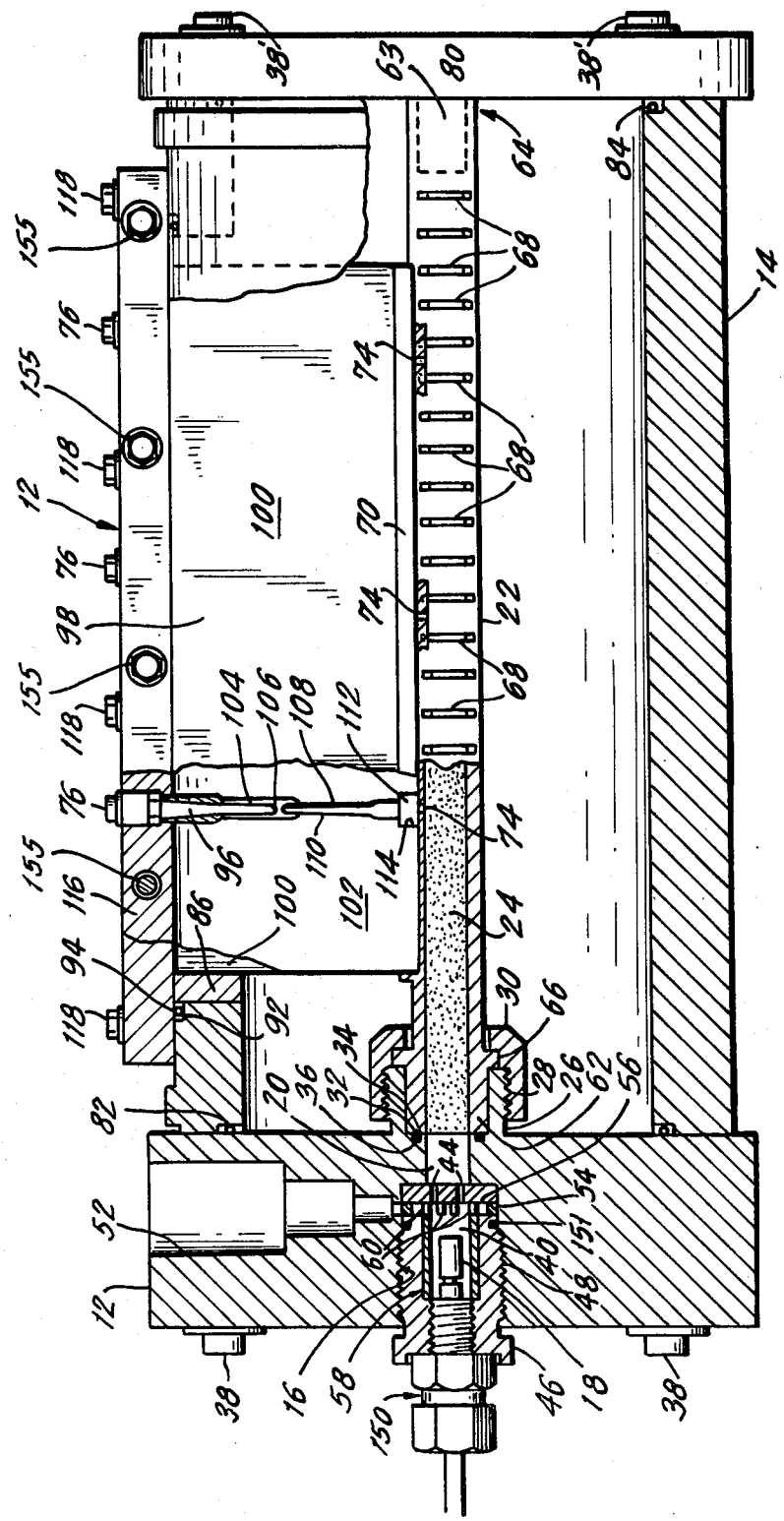

BLACK POWDER FLAMESPREAD TESTER

GOVERNMENTAL INTEREST

The invention herein was made in the course of a contract with the Government and may be manufactured, used and licensed by or for the Government for governmental purposes without the payment to us of any royalties thereon.

BACKGROUND OF THE INVENTION

The present invention pertains generally to apparatus for testing the combustive properties of black powder, and pertains more specifically to apparatus for doing so by measuring the flamespread in a black powder sample.

There are several possible approaches to the determination of the black powder function that also lend themselves to the idea of a single end-of-the-line qualification test. This function can be tracked in a tester by measuring any one of six parameters. First, it is possible to monitor the rate of change of the pressure in a surrounding chamber into which hot gases are emitted from the sample tube. (As is well known, the function of the sample tube, which simulates a primer tube, is to emit hot gases at predetermined rates $m(n,t)$ at each of n orifices as a function of time t.) This measurement in effect actually sums the mass flows from all of the orifices. Second, the rate of advance of the pressure wave in a packed bed of inert propellant simulant in the surrounding chamber can be measured. This simulates the actual advance of pressure in a live cartridge. Third, the advance of pressure along the sample tube, which is a function of the flamespread rate and of the burning rate of the powder, can be measured. Fourth, the flamespread rate itself can be measured directly. Fifth, the photo-active flash intensity output from each of the n orifices can be monitored as a function of time. Sixth, the heat intensity coming from each orifice can be measured as a function of time by means of fast response heat transfer gauges, each of which measures the output of a respective orifice.

Another possible approach to qualifying black powder would be to measure the relative quickness and/or induction time in a closed bomb-type firing. This approach has the advantage of using well-known equipment and techniques. The flamespread rate can be shown theoretically to be related to powder ignitability, as measured by induction time, and to burning rate, as measured by relative quickness.

However, it is not clear that an apparatus that was really designed to measure the burning rate, and not the flamespread rate, is suitable for use in qualifying black powder for its proper function in a gun. Black powder is not the propelling charge of the gun, and a device that measures relative quickness may therefore not necessarily be measuring the correct functional property of the powder. For example, it is conceivable that a particular powder sample might have a slow burning coating and a fast burning interior. Such a sample, if subjected to a closed bomb-type firing, would show a high relative quickness, although it would have a relatively low flamespread rate. The result of the closed bomb test in such a case might therefore be misleading. For this reason, the conventional closed bomb firing does not appear to be readily adaptable for qualifying black powder.

The six types of measurements listed above, have direct physical significance to the black powder function in a gun. Each of them should therefore theoretically be suitable for the task at hand. Not all of these methods, however, appear to be equally simple, reliable and free of error. We have determined that overall, the direct determination of the flamespread rate itself is the most advantageous approach.

SUMMARY OF THE INVENTION

It is the principal object of this invention to provide a black powder flamespread tester for qualifying black powder simply and reliably.

It is another object of the invention to provide a black powder flamespread tester that is suitable for testing black powder of Class 1 and Class 3 granulation.

It is a further object of the invention to provide a black powder flamespread tester than can achieve the foregoing objectives economically, and with little or no likelihood of error.

According to the present invention, the foregoing objects are attained by means of an apparatus in which a verticallyoriented packed bed of sample black powder is ignited at its upper end, and in which a plurality of light sensors disposed along the length of the black powder sample tube is employed to monitor the flamespread through the sample as a function of time. In the preferred embodiments, the packed bed of sample black powder is contained in a steel sample tube housed within a stainless steel tester chamber. The sample tube is provided with rows of slots to allow the escape of the combustion gases into the tester chamber, from which they are continuously vented to the atmosphere (a slow gas bleed). The tester chamber can either be employed as a plenum chamber (i.e. be filled with air at atmospheric pressure) during the firing test, or contain inert propellant simulant to establish a pressure gradient in the chamber during the test.

The vertical orientation of the sample bed minimizes flamespread velocity data randomness that may occur as a result of possible movement of the sample bed in other orientations, e.g. horizontal orientation.

Ignition of the black powder sample is accomplished by means of an electrically activated pyrotechnic squib. In order to minimize randomness in the flamespread velocity due to variations in gas production rate of the squib, the squib is contained in a specially designed transition chamber that serves to "integrate" the gas flowing from the squib to the black powder bed. An orifice plate separates the transition chamber from the powder bed and is provided with a plurality of orifices to allow the passage of the gas from the transition chamber to the bed. By altering the volume of the transition chamber and/or the diameter of the orifices, the characteristic chamber length, L* can be modified to tailor the igniter p-t signature. L* is equal to the transition chamber volume divided by the total orifice area of the orifice plate. The igniter assembly is equipped with a mounting port for a pressure transducer, to permit the transition chamber pressure to be monitored.

Hot gases from the squib igniter are metered through the orifices, which are preferably four in number and each of diameter equal to 0.093 inch, provided in the igniter orifice plate at the downstream end of the transition chamber in the igniter assembly, and flow into a small void volume provided immediately between the orifice plate and the black powder bed. The void volume helps produce smoother, more reproducible ignition of the black powder bed.

In the preferred embodiment, the light sensor fin comprises three light sensors, which may preferably be photo-transistor light sensors. These three light sensors are equally spaced along the axial length of the powder bed, preferably 3.00 inches apart. The first, i.e. upstream, light sensor, however, is located a distance downstream from the void volume equal to seven times the diameter of the powder bed. This spacing in practice is preferably somewhat greater than the spacing between adjacent light sensors, e.g. 3.25 inches. This feature allows the flame front to stabilize before the first flamespread datum is taken by the first light sensor.

As the flame front passes the first light sensor (which preferably has a peak sensitivity at a wavelength equal to 0.9 $\mu$m), it becomes fully conductive, and the signal generated by the light sensor increases by a one volt d.c. step. When the flame front reaches the second light sensor, it also becomes fully conductive, and its output voltage also increases by one volt d.c. The same thing happens as the flame front passes the third light sensor. The instantaneous outputs from the three light sensors are continuously summed, their sum being the final output of the tester circuitry. Thus, the value of the output voltage at a given instant indicates the number of light sensors which the flame front has passed as of that instant, and a plot of the output voltage versus time reveals the flamespread rate, which is determined for each interval by simply dividing the light sensor spacing by the time between the steps in the output voltage.

Other objects and features of the invention will be apparent from the following description and the accompanying drawings.

BRIEF DESCRIPTION OF THE FIGURES

FIG. 2 is a cross-sectional view of a first preferred embodiment of the flamespread tester of the invention.

DETAILED DESCRIPTION OF THE PREFERRED EMBODIMENTS

The major components of the system are: the variable L* igniter head assembly; the sample tube mounted to the igniter head; the light sensor assembly; and the flamespread tester chamber, which houses the sample tube and receives the light sensor fin assembly.

Ignition System: Variable L* Igniter Head Assembly

Figure 1:
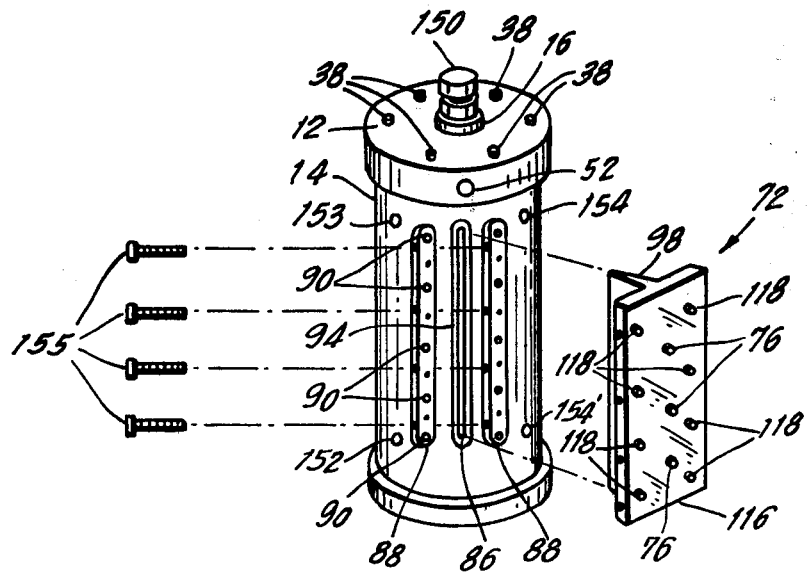
FIG. 1 is a partly exploded view of the preferred embodiment of the flamespread tester of the invention.
Figure 3:
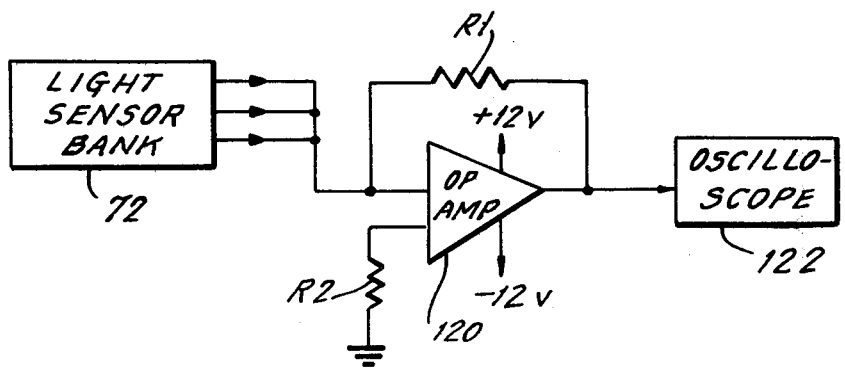
FIG. 3 is a schematic diagram of the circuitry used to analyze the signals generated by the light sensor bank.

In the preferred embodiment shown in FIGS. 1 and 2, the variable L* igniter head 12 is a two-inch thick, six-inch diameter disc made preferably of 304 stainless steel. The igniter head 12 acts as a closure for the upper end of the flamespread tester chamber 14 that houses the ignition system. A first threaded bore hole 16 (FIG. 2) is provided in the upper surface of the igniter head 12 and receives a pyrotechnic initiator 18, which is preferably a *Cartridge Actuated Devices, Inc.* (C.A.D.) Electric Squib type 071023 mounted on a Conax gland assembly 150. The squib 18 can be removed from the first bore 16 for a purpose described below. A 0.4375-inch diameter bore hole 20 (FIG. 2) is located at the center of the downstream side of the igniter head 12 and communicates with the first bore hole 16. The second bore hole 20 allows hot gases from the C.A.D. electric squib to flow into the sample tube 22 and ignite a packed bed of black powder 24 contained therein. The underside of the igniter head 12 (i.e. the side facing the flamespread tester chamber 14) is provided with a cylindrical mounting stud 26, which is preferably also made of 304 stainless steel and which is permanently secured to the igniter head 12. The outer diameter of the mounting stud 26 is machined with 1¼-18 UNF-2A threads 28, onto which a mounting nut 30 for the sample tube 22 is screwed. The mounting stud 26 is coaxial with the first and second bores 16 and 20, and has an inner diameter greater than the diameter of the second bore 20. An annular shoulder 32 is thus defined between the inner diameter of the mounting stud and the mouth of the second bore 20. An annular recess 34 is formed in this shoulder, and an O-ring 36 is provided in the recess to seal against combustion pressure. In the preferred embodiment shown, six bolt clearance holes, preferably of ⅜-inch diameter, are provided equally spaced about the circumference of the igniter head 12 and receive bolts 38 for mounting the igniter head 12 to the flamespread tester chamber 14.

In order to minimize randomness of the measured flamespread rate due to variations in the firing action time of the squib 18, a small transition chamber 40 is provided in the igniter head assembly 12 between the squib initiator 18 and the black powder sample tube 22. The cylindrical transition chamber 40 is defined within the cylindrical structure containing the squib 18, and the squib itself is centered axially in the upper portion of the transition chamber 40. An orifice plate 42 is provided between the transition chamber 40 and the second bore 20. The gas produced by the squib 18 passes from the transition chamber 40, through a plurality of orifices 44 in the orifice plate 42, and through the second bore 20 to reach the black powder bed 24 in the sample tube 22. The second bore 20 serves as a void volume to smooth out irregularities in the flow of the combustion gases as they emerge from the orifice 44. By varying the volume of the transition chamber 40 and the diameter of the orifices 44 of the orifice plate 42 in a manner to be described shortly, it is possible to control precisely the peak transition chamber pressure and the gas particle stay time (which is related to the chamber depressurization time). In this manner an ideal ignition system which minimizes the randomness of the flamespread rate in the packed bed 24 of black powder can be achieved.

The orifice diameter of orifices 44 is controlled by substituting different igniter orifice plates having orifices of different diameter. It has been found especially convenient to provide three igniter orifice plates for the variable L* igniter head assembly. Each orifice plate 42 is a disc made of 1018 mild steel, 0.932-inch in diameter and 0.185-inch thick with four bore holes having their centers equally spaced about a circle of 0.2 inch diameter that is coaxial with the disc. Table 1 sets forth the characteristic residence time, the orifice diameter and the total orifice area of three orifice plates suitable for use with a transition chamber having a volume of 0.229 cubic inch. By using orifice plate #1, relatively fast ignition can be achieved, while orifice plate #3 produces relatively slow ignition.

TABLE 1

| ORIFICE PLATE NO. | CHARACTERISTIC RESIDENCE TIME (msec) | ORIFICE DIAM. (in.) | TOTAL ORIFICE AREA (in.$^2$) |
|---|---|---|---|
| 1 | 0.75 | 0.093 | 0.0270 |
| 2 | 1.50 | 0.063 | 0.0136 |
| 3 | 3.00 | 0.046 | 0.0068 |

The cylindrical structure 46 defining the igniter transition chamber 40 is mounted in the igniter head 12 by means of 1-20 UNEF-2 threads 48. The structure 46 is made of 1018 mild steel, preferably, and has ¼ NPT internal threads 50 to accept the Conax gland carrying the C.A.D. electric squib 18. The igniter transition chamber inner diameter is preferably 0.563 inch. The bottom face (right-hand face in FIG. 2) of the transition chamber 40 abuts the igniter orifice plate 42 when the transition chamber structure 46 is tightened into place. A circumferential groove is formed in the outer surface of the transition chamber structure 46, 0.13 inch back from the bottom face. An O-ring 151, preferably a Parker #2-116-N674-70, is provided to seal against combustion pressure.

A pressure transducer port 52 is machined into the cylindrical peripheral surface of the igniter head 12 to accept a transducer mounting adapter (not shown), which is preferably a ⅜-24 UNF-2A adapter, e.g. Kristal type 6504.

A collecting ring 54 and radial slots 56 are machined into the bottom end of the transition chamber structure 46 to communicate pressure to a pressure transducer (not shown) in the transducer port 52.

The volume of the transition chamber 40 may be varied by the insertion of a sleeve insert 58. It has been found especially convenient to provide two such sleeve inserts, preferably machined from 1018 mild steel. Each insert is 1.0 inch long and has an outer diameter of 0.562 inch. One end of each insert 58 is machined with radial slots 60 to permit the transition chamber 40 to communicate with the transducer port 52. Table 2, below, sets forth the dimensions of the transition chamber 40 with no insert, with the first insert and with the second insert.

TABLE 2

| IGNITER SLEEVE INSERT | TRANSITION CHAMBER PRESSURE (psi) | TRANSITION CHAMBER DIAMETER (in.) | TRANSITION CHAMBER VOLUME (in.$^3$) |
|---|---|---|---|
| None | 500 | 0.563 | 0.229 |
| #1 | 1000 | 0.375 | 0.114 |
| #2 | 1500 | 0.313 | 0.076 |

By appropriate choice of the sleeve insert and the igniter orifice plate, the L* value of the igniter system can be varied to provide the desired ignition profile. For Class 1 black powder we have determined that the flamespread rate randomness is minimized by using no sleeve insert in the transition chamber, and using igniter orifice plate #1, in which the orifice diameter is 0.093-inch.

Sample Tube

As noted above, a tubular sample holder 22 is provided to contain the black powder sample 24. The sample tube 22 is preferably made of 1018 steel, and has a length of 10.2 inches and a 7/16-inch diameter bore along its entire length. The lower end 64 of the sample tube 22 is closed via a 9/16-12 UNC threaded plug 63.

The nominal loading of black powder in the sample tube is 25 grams, with some variation depending on the class of black powder and the packing density.

The upper end 62 of the sample tube 22 is open and fits into the interior of the mounting stud 26 and communicates with the void volume 20, via which the hot igniter gases enter the sample tube 22 and initiate burning of the black powder bed 24. An annular flange 66 is preferably provided 21/32 inch down from the upper end 62 of the sample tube 22 on its outer surface. The cylindrical sample tube mounting nut 30, the interior surface of which is threaded, is fitted over the bottom end of the sample tube 22 after the latter has been put in place, and is screwed onto the mounting stud 26 to hold the sample tube 22 firmly in place. The face of the upper end 62 of the sample tube contacts the annular shoulder 32 and seals against the O-ring 36 when the mounting nut 30 is tightened onto the mounting stud 26.

The preferred embodiment of the sample tube 22, shown in FIG. 2, is suitable for testing both Class 1 and Class 3 granule classes of black powder without the need for a liner sleeve. The sample tube 22 is provided with a plurality of circumferential slots 68, each of which is 0.045 inch wide (in the direction of the axis of the sample tube 22) and 0.40 inch long (in the direction of the circumference of the sample tube 22). The sample tube 22 is provided with forty-four slots 68, which are arranged in two identical rows of twenty-two slots 68 each, each row extending along the length of the tube 22. The corresponding slots 68 of the two rows are located 180° apart from each other about the circumference of the sample tube 22. Since granules cannot easily plug a long, narrow slot, randomness in the measured flame-spread rate is kept low with this embodiment.

The sample tube 22 has a 45° dovetailed groove 70 (FIG. 2) with a ⅜-inch base machined along the length of the tube 22 on one side for attachment of the light sensor bank 72, as described below. Several small sight holes 74 (FIG. 2) aligned with light sensor output ports 76, equal in number to the number of light sensors used (three in the preferred embodiment illustrated), are drilled through the tube wall at the base of the dovetailed groove 70. Each of the sight holes 74 is preferably 0.055 inch in diameter. The sight holes 74 are so positioned that when the light sensor bank 72 is assembled with the tester chamber 14, the igniter head assembly 12 and the sample tube 22 as shown in FIG. 2 and described below, each light sensor 76 is exactly aligned with a respective sight hole 74. In the preferred embodiment shown, the first (top) sight hole 74 is located 3.25 inches down from the upper end 62 of the sample tube 22, the second sight hole 74 is 3.00 inches center-to-center from the first, and the third is 3.00 inches center-to-center from the second.

Flamespread Tester Chamber

The flamespread tester chamber 14 is a cylindrical body machined preferably from type 304H XX-strong seamless stainless steel pipe, and preferably has an inner diameter of 4.06 inches, an outer diameter of 5.400 inches and a length of 11.9 inches. Each end of the chamber 14 is provided with six equally spaced axial 5/16-inch-18 UNC-2B threaded bolt holes. The upper end of the flamespread tester chamber 14 is closed by means of the variable L* igniter head assembly 12, which is provided with six bolt clearance holes corresponding to the six threaded bolt holes in the upper end of the tester chamber 14. The lower end of the tester chamber 14 is closed by means of a disc-shaped chamber head 80, which is provided with six bolt clearance holes corresponding to the six threaded bolt holes in the lower end of the tester chamber 14. The igniter head 12 and the chamber head 80 are each fastened to the chamber 14 by means of six high strength 5/16-18 UNC×2-½-inch long socket head cap screws 38, 38' with washers. Each end of the tester chamber 14 is machined to accept an O-ring 82, 84 for sealing the chamber pressure. In the preferred embodiment shown, a Parker #2-156-N 674-70 O-ring is used at each end of the chamber 14.

A milled axial slot 86 that is 8.45 inches long is provided in the flamespread tester chamber wall to receive the light sensor bank 72, as illustrated in FIGS. 1 and 2 and described below. Two clamping bars 88 are provided on the exterior of the tester chamber wall (see FIG. 1) to secure the light sensor bank 72 to the chamber 14. Each clamping bar 88 is preferably at least equal in length to the light sensor bank 72, and is preferably made of 1018 steel. Each bar 88 is secured to the wall of the flamespread tester chamber 14 by means of five 5/16-18 UNC-2B bolts 90. A groove 92 is provided on the outer surface of the tester chamber wall surrounding the slot 86 and receives a sealing O-ring 94.

The flamespread tester chamber 14 is also provided with two ⅛ NPT threaded holes 152 and 153 (FIG. 1) for connection of purge inlet and vent lines, respectively (not shown). The holes for the vent 153 and the purge inlet 152 are located 1.53 and 9.98 inches down from the upper end of the tester chamber 14, respectively, and 45° circumferentially to the left of the centerline of the milled axial slot 86. Two ⅜-24 UNF mounting holes 154, 154' are provided in the wall of the chamber to receive Kristal type 601-A quartz pressure transducers. The two transducer mounting holes 154, 154' are located 1.53 inches and 9.98 inches down from the upper end of the tester chamber 14 and 45° circumferentially to the right of the centerline of the milled slot 86. The preferred embodiment of the chamber has been successfully hydrotested to 1140 psi without permanent deformation or failure.

During a test, the combustion gases are vented from the sample tube 22 into the tester chamber 14 via the slots 68 (FIG. 2). Since these combustion products coat the interior wall of the tester chamber 14, the interior wall must be cleaned between tests.

Light Sensor Assembly

The light sensor bank 72, which is used to measure the flamespread rate in the bed 24 of black powder, preferably comprises three light sensors 96 having respective outlet ports 76. Each sensor 96 contains an NPN planar silicon phototransistor 104, such as Texas Instruments type LS 400. The three phototransistors 104 are mounted in a row in a fin-like housing 98 that comprises two facing walls 100, 102 (FIG. 2) and that projects into the flamespread tester chamber 14 through the aperture 86 and mates with the dovetailed groove 70 of the sample tube 22. In FIG. 2, a portion of one wall 100 is broken away to allow a view of the uppermost light sensor 96. The three light sensors 96 are spaced equal distance, preferably 3.0 inches, apart from each other in the housing 98. The first light sensor 96 is located a distance from the top end 62 of the sample tube 22 equal to at least seven times the inner diameter of the tube 22. In the preferred embodiment shown, this distance is 3.25 inches. This spacing ensures that ignition irregularities will not be detected by the light sensors 96. Such detection could cause an erroneous determination of the flamespread rate.

Each of the three Texas Instruments LS 400 phototransistors 104 measures approximately 0.080 inch in diameter and 0.60 inch long, with two 0.010-inch diameter lead wires 1.5 inches long which extend to their respective outlet port 76. The active chip is mounted on a ceramic pedestal and encased in glass. The glass body has a dome-shaped focusing lens 106 over the chip. A red dot on the body identifies the collector lead. The collector lead is connected to the center contact of preferably an RCA phonoplug receptacle 76. The emitter lead is connected to the coaxial contact of the receptacle. The typical rise time of these devices is 8 microseconds with a 6-microsecond fall time. The peak sensitivity of these devices is in the rear infrared at a wavelength of approximately 0.9 micrometer, which makes them well suited for flame detection.

Each phototransitor 104 is isolated from the combustion pressure in the sample tube 22 by means of a respective pressure sealing optic rod 108, only one of which is shown. Each of these rods 108 is beaded at one end and potted into the light sensor housing 98 with epoxy, the beaded end 110 oriented toward the sample tube 22. In order to protect these glass rods 108 from the hot combustion products, a sacrificial window 112 made of acrylic plastic is glued into a milled slot 114 in the bottom edge of the light sensor bank housing 98 beneath each light sensor 96. These windows 112 must be replaced after each test.

The light sensor bank housing 98 is preferably made of yellow brass and is machined with a male dovetail to match the corresponding groove 70 in the sample tube 22, as noted above. The length of the groove 70 in the sample tube 22 is such that when the sample tube 22 and the light sensor bank 72 are mated, the light sensors 96 are automatically aligned with the sight holes 74 provided in the sample tube 22 to permit the measurement of changes in luminosity associated with flame front passage. The light sensor bank housing 98 has a top flange 116 which is joined to the fin-like portion 98 of the housing at a right angle. The flange 116 is secured to each of the two clamping bars 88 by means of four high strength 5/16-18 UNC×3-inch socket head cap screws 155 with washers. The clearance holes in the top flange 116 which receive these screws are bored perpendicular to the axial centerline and have a diameter of 0.348 inch. The flange 116 is secured to the tester chamber 14 by means of eight #10-24 UNC×¾-inch socket head cap screws 118 with washers. As noted above, a pressure seal between the flange 116 of the light sensor bank 72 and the tester chamber 14 is provided by means of a Parker #2-163-N674-70 O-ring 94.

The phototransistors 104 become fully conductive when subjected to 9 mW/cm² of radiant energy. This is such a small amount of radiant energy that each light sensor 96 becomes completely saturated substantially concurrently with the passage of the flame front past the corresponding sight hole 74. The collector of each phototransistor 104 is connected to a summing operational amplifier 120, the output of which is set at −8 volts d.c. via resistor R1 before the beginning of the test, when the phototransistors 104 are all in the "dark" or non-conductive state. As the flame front passes each of the sight holes 74, the output of the corresponding phototransistor 104 rises to its saturation level of 1 volt d.c., resulting in a corresponding 1-volt step rise of the operational amplifier output. The output of the op amp 120 is preferably displayed on an oscilloscope 122, or any suitable high-speed recording/display system. Amplifier 120 may be a type 741 operation amplifier. Resistor R1 connected to pin 2 is a 36K resistor and resistor R2 connected to pin 3 is a 1K resistor. As shown in FIG. 4B, the plot of the op amp 120 output voltage versus time (curve A) has the form of a series of step increases in the output from the initial level −8 volts d.c. to a final level of −5 volts d.c. (in the case where three light sensors are employed). The distance between any two consecutive steps is directly proportional to the time required for the flame front to cover the distance between the two corresponding sight holes 74 in the sample tube 22. Division of the distance between each two adjacent sight holes 74 by the time interval between the corresponding steps in the plotted graph will give the average speed of the flame front between the two holes in question. In the example shown in FIG. 4B, an interval of approximately 6 milliseconds was required for the flame front to proceed from the first sight hole 74 to the second, and an additional 8 milliseconds were required for the flame front to reach the third sight hole 74.

The circuitry is preferably designed to accept input lead wires from as many as eight phototransistors, preferably using RCA-type phonoplugs (not shown). The output connector is a BNC positive type. The circuit is designed to operate on standard 120-volt a.c. power line with a three-wire grounded plug and is preferably protected with a three ampere AGC fuse (not shown).

Figure 4A:
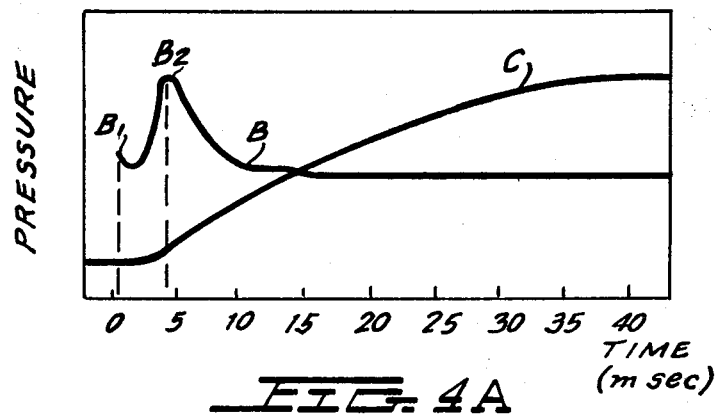
FIG. 4A and FIG. 4B show oscilloscope displays of the plots of the signals produced by the circuitry of FIG. 3 and of other signals produced by the flamespread tester of the invention.
Figure 4B:
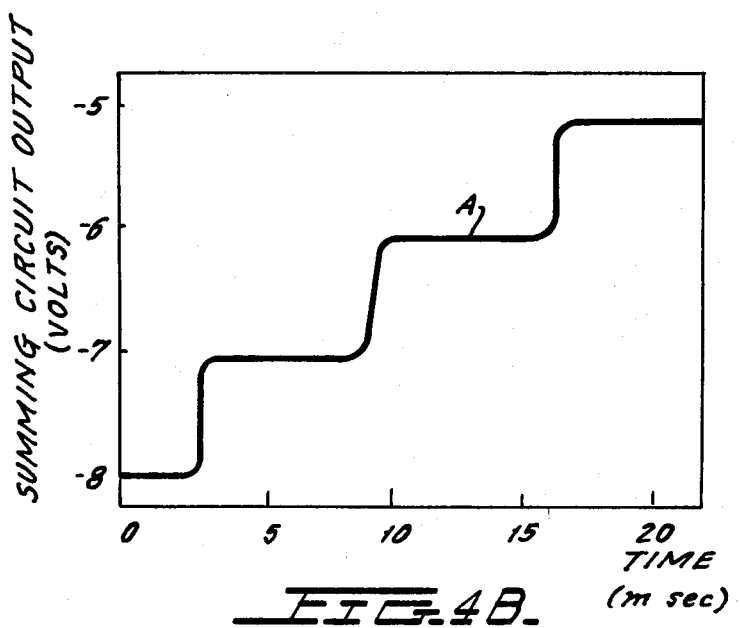

FIG. 4A also shows plots of the output of the pressure transducers. Curve B is a plot showing the pressure in the igniter transition chamber as a function of time. Peak B1 represents the peak pressure in the transition chamber due to the squib ignition (igniter orifices choked). Peak B2 represents the peak pressure in the transition chamber due to the black powder combustion (igniter orifices unchoked). Curve C is a plot of the tester chamber pressure versus time.

The present invention may be embodied in other specific forms without departing from the spirit or essential attributes thereof and, accordingly, reference should be made to the appended claims, rather than to the foregoing specification, as indicating the scope of the invention.

What is claimed is:

1. A black powder flamespread tester, said tester comprising:
    sample holding means for holding a sample of black powder to be tested;
    ignition means for igniting a sample contained in said sample holder means, said ignition means including;
    an electrically actuated pyrotechnic squib;
    an ignition head having a first bore formed therein, said squib being received in said first bore, a transition chamber defined in said ignition head, said squib emitting hot gases into said transition chamber upon actuation, and a void volume operatively disposed in said ignition head, said gases from said squib passing from said transition chamber via said void volume into said sample holding means to ignite a sample contained in said sample holding means, passage of said gases through said void volume serving to smooth the flow of said gases;
    said ignition means further including an orifice plate disposed between said transition chamber and said void volume, said orifice plate having a plurality of orifices formed therein for metering said gases from said transition chamber to said void volume; and
    said tester further comprising optical monitoring means for measuring the rate at which a flame front propagates through a sample contained in said sample holding means when the sample is ignited by said ignition means.

2. The tester of claim 1, wherein said ignition means further comprises a plurality of sleeve inserts, one said sleeve insert being selectively removably received in said transition chamber to decrease the size of said transition chamber, for modifying the ignition characteristics of said ignition means for a particular test.

3. The tester of claim 1, wherein a plurality of orifice plates is selectively and removably disposable between said transition chamber and said void volume, whereby orifice plates each of different respective sizes can be selectively inserted between said transition chamber and said void volume for a particular test to control the flow properties of said gases in order to control the ignition characteristics of said ignition means.

4. The tester of claim 1, wherein said ignition head has pressure transducer port means defined therein for receiving a pressure transducer for monitoring the pressure in said transition chamber.

5. The tester of claim 1, wherein said optical monitoring means comprises a plurlity of light sensor means, each said light sensor means continuously generating an electrical signal representative of the amount of light being received by it at each instant during the testing of a sample.

6. The tester of claim 5, wherein said sample holding means comprises sample tube means having a plurality of sight holes formed therein, each said light sensor means being aligned with a respective said sight hole.

7. The tester of claim 5, further comprising summing circuit means for summing the signals generated by said light sensor means and for generating an output signal representative of the sum of said signals, said output signal being representative of the number of said light sensor means that a wave front propagating in a sample contained in said sample holding means has passed as of a given instant.

8. The tester of claim 7, wherein said summing circuit means comprises an operational amplifier, said operational amplifier producing said output signal.

9. The tester of claim 5 or claim 7, wherein each said light sensor means comprises a phototransistor.

10. The tester of claim 9, wherein each said phototransistor has a maximum sensitivity to radiation having a wavelength of approximately 0.9 micrometer.

11. The tester of claim 6, wherein each of said sight holes has a respective sacrificial window thereacross to at least partly shield its respective light sensor means from products of the ignition of said sample.

12. The tester of claim 5, wherein said optical monitoring means further comprises a housing containing said light sensor means.

13. The tester of claim 12, further comprising tester chamber means containing said sample holding means, said tester chamber means having an aperture formed therein for removably receiving said housing of said optical monitoring means.

14. The tester of claim 13, wherein said housing comprises a fin-shaped part for being received in said aperture.

15. The tester of claim 14, wherein said sample holder means has a dovetailed groove defined on an outer surface thereof, said fin-shaped part of said housing being adapted to mate with said groove when received in said aperture.

16. The tester of claim 5, further comprising tester chamber means containing said sample holding means.

17. The tester of claim 16, wherein said sample holding means has apertures formed therein for venting combustion gases into said tester chamber means.

18. The tester of claim 17, wherein said sample holding means is tubular and said apertures comprise two rows of circumferential slots 180° apart disposed along at least a portion of the length of said sample holding means.

19. The tester of claim 16, wherein said ignition means comprises an ignition head that is adapted to be removably secured to said tester chamber means for testing a sample, and that is also adapted to have said sample holding means secured to it within the interior of said tester chamber means.

20. The tester of claim 16, wherein said tester chamber means has at least one pressure transducer port defined therein for receiving a pressure transducer for monitoring the pressure within said tester chamber means.

21. The tester of claim 11, which further includes respective optical rod means optically coupling said sacrificial window to said phototransistor.

* * * * *